US008604255B2

(12) United States Patent
Sarager et al.

(10) Patent No.: US 8,604,255 B2
(45) Date of Patent: Dec. 10, 2013

(54) PROCESS FOR RECOVERING ETHANOL WITH SIDEDRAWS TO REGULATE $C_{3+}$ ALCOHOLS CONCENTRATIONS

(75) Inventors: Lincoln Sarager, Houston, TX (US); Al Amleh, Pearland, TX (US); Trinity Horton, Houston, TX (US); Radmila Jevtic, Pasadena, TX (US); Victor J. Johnston, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 286 days.

(21) Appl. No.: 13/078,742

(22) Filed: Apr. 1, 2011

(65) Prior Publication Data

US 2012/0010442 A1    Jan. 12, 2012

Related U.S. Application Data

(60) Provisional application No. 61/332,696, filed on May 7, 2010.

(51) Int. Cl.
*C07C 29/74* (2006.01)
*C07C 29/149* (2006.01)

(52) U.S. Cl.
USPC .......................................... 568/885; 568/913

(58) Field of Classification Search
USPC ................................................ 568/885, 913
See application file for complete search history.

(56) References Cited

U.S. PATENT DOCUMENTS

| | | |
|---|---|---|
| 2,649,407 A | 8/1953 | Harrison |
| 2,702,783 A | 2/1955 | Harrison |
| 2,801,209 A | 7/1957 | Muller et al. |
| 2,882,244 A | 4/1959 | Milton |
| 3,130,007 A | 4/1964 | Breck |
| 3,408,267 A | 10/1968 | Miller |
| 3,445,345 A | 5/1969 | Adam |
| 3,478,112 A | 11/1969 | Adam |
| 3,990,952 A | 11/1976 | Katzen |
| 4,275,228 A | 6/1981 | Gruffaz |
| 4,306,942 A | 12/1981 | Brush |
| 4,317,918 A | 3/1982 | Takano |
| 4,319,058 A | 3/1982 | Kulprathipanja |
| 4,379,028 A | 4/1983 | Berg |
| 4,395,576 A | 7/1983 | Kwantes |
| 4,398,039 A | 8/1983 | Pesa |
| 4,421,939 A | 12/1983 | Kiff |
| 4,422,903 A | 12/1983 | Messick |
| 4,454,358 A | 6/1984 | Kummer et al. |
| 4,465,854 A | 8/1984 | Pond |
| 4,471,136 A | 9/1984 | Larkins |
| 4,480,115 A | 10/1984 | McGinnis |
| 4,492,808 A | 1/1985 | Hagen |
| 4,497,967 A | 2/1985 | Wan |
| 4,520,213 A | 5/1985 | Victor |
| 4,541,897 A | 9/1985 | Sommer |
| 4,592,806 A | 6/1986 | Ilgner et al. |
| 4,626,321 A | 12/1986 | Grethlein |
| 4,678,543 A | 7/1987 | Houben |
| 4,692,218 A | 9/1987 | Houben |
| 4,777,303 A | 10/1988 | Kitson |
| 4,804,791 A | 2/1989 | Kitson |
| 4,842,693 A | 6/1989 | Wheldon |
| 4,961,826 A | 10/1990 | Grethlein |
| 4,985,572 A | 1/1991 | Kitson |
| 4,990,655 A | 2/1991 | Kitson |
| 4,994,608 A | 2/1991 | Torrence et al. |
| 5,001,259 A | 3/1991 | Smith et al. |
| 5,026,908 A | 6/1991 | Smith et al. |
| 5,035,776 A | 7/1991 | Knapp |
| 5,061,671 A | 10/1991 | Kitson |
| 5,124,004 A | 6/1992 | Grethlein |
| 5,144,068 A | 9/1992 | Smith et al. |
| 5,149,680 A | 9/1992 | Kitson |
| 5,185,481 A | 2/1993 | Muto |
| 5,198,592 A | 3/1993 | vanBeijnum |
| 5,215,902 A | 6/1993 | Tedder |
| 5,227,141 A | 7/1993 | Kim |
| 5,233,099 A | 8/1993 | Tabata |
| 5,237,108 A | 8/1993 | Marraccini |
| 5,250,271 A | 10/1993 | Horizoe |
| 5,284,983 A | 2/1994 | Muto et al. |
| 5,342,488 A | 8/1994 | Gosch et al. |
| 5,348,625 A | 9/1994 | Berg |
| 5,415,741 A | 5/1995 | Berg |
| 5,437,770 A | 8/1995 | Berg |
| 5,445,716 A | 8/1995 | Berg |
| 5,449,440 A | 9/1995 | Rescalli |
| RE35,377 E | 11/1996 | Steinberg et al. |

(Continued)

FOREIGN PATENT DOCUMENTS

| | | |
|---|---|---|
| DE | 19914260 | 10/2000 |
| EP | 0056488 | 7/1982 |

(Continued)

OTHER PUBLICATIONS

Written Opinion mailed May 8, 2012 in corresponding International Application No. PCT/US2011/035586.

(Continued)

*Primary Examiner* — Sikarl Witherspoon

(57) ABSTRACT

Purification and/or recovery of ethanol from a crude ethanol product obtained from the hydrogenation of acetic acid. Separation and purification processes of a crude ethanol mixture are employed to allow recovery of ethanol and remove impurities. In particular, the process involves one or more sidedraws to regulate $C_3+$ alcohols concentration in the recovered ethanol.

23 Claims, 3 Drawing Sheets

(56) References Cited

U.S. PATENT DOCUMENTS

| | | |
|---|---|---|
| 5,599,976 A | 2/1997 | Scates et al. |
| 5,762,765 A | 6/1998 | Berg |
| 5,800,681 A | 9/1998 | Berg |
| 5,821,111 A | 10/1998 | Gaddy et al. |
| 5,993,610 A | 11/1999 | Berg |
| 6,121,498 A | 9/2000 | Tustin |
| 6,143,930 A | 11/2000 | Singh et al. |
| 6,232,352 B1 | 5/2001 | Vidalin et al. |
| 6,294,703 B1 | 9/2001 | Hara |
| 6,375,807 B1 | 4/2002 | Nieuwoudt |
| 6,509,180 B1 | 1/2003 | Verser et al. |
| 6,627,770 B1 | 9/2003 | Cheung et al. |
| 6,657,078 B2 | 12/2003 | Scates et al. |
| 6,685,754 B2 | 2/2004 | Kindig et al. |
| 6,693,213 B1 | 2/2004 | Kolena et al. |
| 6,723,886 B2 | 4/2004 | Allison |
| 6,906,228 B2 | 6/2005 | Fischer et al. |
| 6,927,048 B2 | 8/2005 | Verser et al. |
| 7,005,541 B2 | 2/2006 | Cheung et al. |
| 7,115,772 B2 | 10/2006 | Picard et al. |
| 7,208,624 B2 | 4/2007 | Scates et al. |
| 7,297,236 B1 | 11/2007 | VanderGriend |
| 7,375,049 B2 | 5/2008 | Hayes |
| 7,399,892 B2 | 7/2008 | Rix |
| 7,507,562 B2 | 3/2009 | Verser et al. |
| 7,518,014 B2 | 4/2009 | Kimmich |
| 7,553,397 B1 | 6/2009 | Colley |
| 7,572,353 B1 | 8/2009 | VanderGriend |
| 7,585,339 B2 | 9/2009 | Dahl |
| 7,608,744 B1 | 10/2009 | Johnston et al. |
| 7,732,173 B2 | 6/2010 | Mairal |
| 7,744,727 B2 | 6/2010 | Blum et al. |
| 7,863,489 B2 | 1/2011 | Johnston et al. |
| 2006/0019360 A1 | 1/2006 | Verser |
| 2007/0270511 A1 | 11/2007 | Melnichuk |
| 2008/0135396 A1 | 6/2008 | Blum |
| 2009/0014313 A1 | 1/2009 | Lee |
| 2009/0023192 A1 | 1/2009 | Verser |
| 2009/0081749 A1 | 3/2009 | Verser |
| 2009/0166172 A1 | 7/2009 | Casey |
| 2009/0221725 A1 | 9/2009 | Chornet |
| 2009/0318573 A1 | 12/2009 | Stites |
| 2010/0029980 A1 | 2/2010 | Johnston et al. |
| 2010/0029995 A1 | 2/2010 | Johnston et al. |
| 2010/0030001 A1 | 2/2010 | Chen et al. |
| 2010/0030002 A1 | 2/2010 | Johnston et al. |
| 2010/0121114 A1 | 5/2010 | Johnston et al. |
| 2010/0197485 A1 | 8/2010 | Johnston et al. |

FOREIGN PATENT DOCUMENTS

| | | |
|---|---|---|
| EP | 0104197 | 4/1984 |
| EP | 0120269 | 10/1984 |
| EP | 0167300 A1 | 1/1986 |
| EP | 0456647 | 11/1991 |
| EP | 0557786 | 9/1993 |
| EP | 2060553 A1 | 5/2009 |
| EP | 2060555 A1 | 5/2009 |
| EP | 2072487 | 6/2009 |
| EP | 2072488 | 6/2009 |
| EP | 2072489 | 6/2009 |
| EP | 2072492 | 6/2009 |
| EP | 2186787 | 5/2010 |
| JP | 4193304 A | 7/1992 |
| WO | WO 83/03409 | 10/1983 |
| WO | WO 2008/135192 | 11/2008 |
| WO | WO 2009/009322 | 1/2009 |
| WO | WO 2009/009323 | 1/2009 |
| WO | WO 2009/048335 | 4/2009 |
| WO | WO 2009/063176 | 5/2009 |
| WO | WO 2010/055285 | 5/2010 |

OTHER PUBLICATIONS

International Search Report and Written Opinion mailed Oct. 6, 2011 in corresponding International Application No. PCT/US2011/035586.

International Preliminary Report on Patentability mailed Jul. 27, 2012 in corresponding International Application No. PCT/US2011/035586.

International Search Report for PCT/US2011/035586, dated Nov. 10, 2011 (4 pages).

English abstract for WO 2008/135192, Nov. 13, 2008.

English abstract for EP0056488, Jul. 28, 1982.

English abstract for EP0120269, Oct. 3, 1984.

English abstract for EP0557786, Sep. 1, 1993.

English abstract for DE19914260, Oct. 5, 2000.

Zheng, et al. (2007). Preparation and catalytic properties of a bimetallic Sn-Pt complex in the supercages of NaY zeolite by use of surface organometallic chemistry, Applied Organometallic Chemistry, 21(10), 836-840.

ZeaChem, Inc., Technology Overview, Lakewood, Colorado www.zeachem.com, 2008.

Santori et al. (2000). Hydrogenation of carbonylic compounds on Pt/SiO2 catalysts modified with SnBu4, Studies in Surface Science and Catalysis, 130, 2063-2068.

Rachmady, Acetic Acid Reduction by H2 on Bimetallic Pt Fe Catalysts, Journal of Catalysis 209, 87-98 (Apr. 1, 2002), Elsevier Science (USA).

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Hilmen, Separation of Azeotropic Mixtures: Tools for Analysis and Studies on Batch Distillation Operation (Nov. 2000) p. 17-20.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Amit M. Goda et al., DFT modeling of selective reduction of acetic acid to acetaldehyde on Pt-based bimetallic catalysts, 20th NAM, Houston, Tx, Jun. 17-22, 2007 available online at < http://www.nacatsoc.org/20nam/abstracts/O-S9-18.pdf>.

Acala, et al., (2005). Experimental and DFT studies of the conversion of ethanol and acetic acid on PtSn-based catalysts, Journal of Physical Chemistry, 109(6), 2074-2085.

PROCESS FOR RECOVERING ETHANOL WITH SIDEDRAWS TO REGULATE $C_{3+}$ ALCOHOLS CONCENTRATIONS

CROSS REFERENCE TO RELATED APPLICATIONS

This application claims priority to U.S. Provisional Application No. 61/332,696, filed on May 7, 2010, the entire content and disclosure of which is incorporated herein by reference.

FIELD OF THE INVENTION

The present invention relates generally to processes for producing and recovering ethanol and, in particular, to processes for recovering ethanol from a crude product from acetic acid hydrogenation that contains $C_{3+}$ alcohols, e.g., heavy alcohols.

BACKGROUND OF THE INVENTION

Ethanol for industrial use is conventionally produced from petrochemical feed stocks, such as oil, natural gas, or coal, from feed stock intermediates, such as syn gas, or from starchy materials or cellulose materials, such as corn or sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are converted to ethanol by fermentation. However, fermentation is typically used for consumer production of ethanol for fuels or consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acid, e.g., acetic acid, other compounds are formed with ethanol or are formed in side reactions. These impurities limit the production and recovery of ethanol from such reaction mixtures. For example, during hydrogenation, esters are produced that together with ethanol and/or water form azeotropes, which are difficult to separate. In addition, when conversion is incomplete, unreacted acid remains in the crude ethanol product, which must be removed to recover ethanol.

EP02060553 describes a process for converting hydrocarbons to ethanol involving converting the hydrocarbons to ethanoic acid and hydrogenating the ethanoic acid to ethanol. The stream from the hydrogenation reactor is separated to obtain an ethanol stream and a stream of acetic acid and ethyl acetate, which is recycled to the hydrogenation reactor.

U.S. Pat. No. 2,801,209 describes production of ethanol from olefin dehydration that uses sidedraws to remove oils that buildup in the columns while recovering ethanol.

Therefore, a need remains for improving the recovery of ethanol from a crude product obtained by reducing alkanoic acids, such as acetic acid, and/or other carbonyl group-containing compounds.

SUMMARY OF THE INVENTION

In a first embodiment, the present invention is directed to a process for recovering ethanol comprising hydrogenating acetic acid in an acetic acid feed stream in the presence of a catalyst to form a crude product and separating at least a portion of the crude product into an intermediate stream comprising one or more $C_2+$ alcohols and a residue comprising acetic acid. The process further comprises separating at least a portion of the intermediate stream in a column into a product distillate comprising ethanol, and one or more sidedraws comprising one or more $C_3+$ alcohols. In one embodiment, the product distillate comprises less than 1000 wppm of the one or more $C_3+$ alcohols.

In a second embodiment, the present invention is directed to a process for recovering ethanol comprising hydrogenating acetic acid in an acetic acid feed stream in the presence of a catalyst to form a crude product, separating at least a portion of the crude product in a first column into a first distillate comprising one or more $C_2+$ alcohols and ethyl acetate, and a first residue comprising acetic acid, and separating at least a portion of the first distillate in a second column into a second distillate comprising ethyl acetate, and a second residue comprising one or more $C_2+$ alcohols. The process further comprises separating at least a portion of the second residue in a third column into a third distillate comprising ethanol, and one or more sidedraws comprising one or more $C_3+$ alcohols.

In a third embodiment, the present invention is directed to a process for recovering ethanol comprising hydrogenating acetic acid in an acetic acid feed stream in the presence of a catalyst to form a crude product, separating at least a portion of the crude product into an intermediate stream comprising one or more $C_2+$ alcohols, and a residue comprising acetic acid, and separating at least a portion of the intermediate stream in a second column into a product distillate comprising ethanol and less than 1000 wppm of one or more $C_3+$ alcohols. In this embodiment, one or more sidedraws are taken from the second column to control the $C_3+$ alcohols concentration in the product distillate.

In a fourth embodiment, the present invention is directed to a process for recovering ethanol, comprising providing a crude product comprising ethanol, acetic acid, water, and one or more $C_3+$ alcohols, wherein the concentration of the one or more $C_3+$ alcohols is less than 8 wt. %, separating at least a portion of the crude product into an intermediate stream comprising ethanol and one or more $C_3+$ alcohols, and a residue comprising acetic acid, and separating at least a portion of the intermediate stream in a column into a product distillate comprising ethanol, one or more sidedraws comprising one or more $C_3+$ alcohols, and a residue comprising water.

BRIEF DESCRIPTION OF DRAWINGS

The invention is described in detail below with reference to the appended drawings, wherein like numerals designate similar parts.

DETAILED DESCRIPTION OF THE INVENTION

The present invention relates to processes for recovering ethanol produced by hydrogenating acetic acid in the presence of a catalyst. There may be additional components present during hydrogenation including acids, esters, aldehydes, and anhydrides, depending on the impurity level of the acetic acid feed. These impurities may be reduced along with acetic acid to produce $C_3+$ alcohols, e.g., heavy alcohols. In addition, side reactions during acetic acid hydrogenation may result in formation of $C_3+$ alcohols. The $C_3+$ alcohols may be formed in minor amounts, e.g., less than 10 wt. %, that when present are withdrawn with the recovered ethanol. This may lead to an ethanol product with levels of $C_3+$ alcohols impurities that may require further processing. The further processing may be inefficient to remove the minor amounts of the $C_3+$ alcohols from the ethanol. Although some $C_3+$ alcohols may be tolerated in certain ethanol applications, such as fuel grade ethanol, it is advantageous to regulate the $C_3+$ alcohols concentration in the recovered ethanol. Embodiments of the present invention overcome the problems associated with $C_3+$ alcohols by providing an efficient process to regulate the amount $C_3+$ alcohols in the recovered ethanol.

For purposes of the present invention, $C_3+$ alcohols are generally referred to as heavy alcohols and comprise alcohol species that have a higher boiling point than ethanol. These alcohols species may also include azeotropes of the $C_3+$ alcohols. The $C_3+$ alcohols have at least three carbons, e.g., at least four carbons or at least five carbons. In terms of ranges, $C_3+$ alcohols include from $C_3$ to $C_6$ alcohols, or more preferably from $C_3$ to $C_5$ alcohols. Examples of $C_3+$ alcohols include isopropanol, n-propanol, n-butanol, 2-butanol, isobutanol, tert-butanol, 2,2-dimethyl-1-propanol, 3-pentanol, 2-pentanol, 1-pentanol, 3-methyl-2-butanol, 2-methyl-2-butanol, mixtures thereof, and azeotropes thereof. In one embodiment, the $C_3+$ alcohols include isopropanol and n-propanol.

Figure 1:
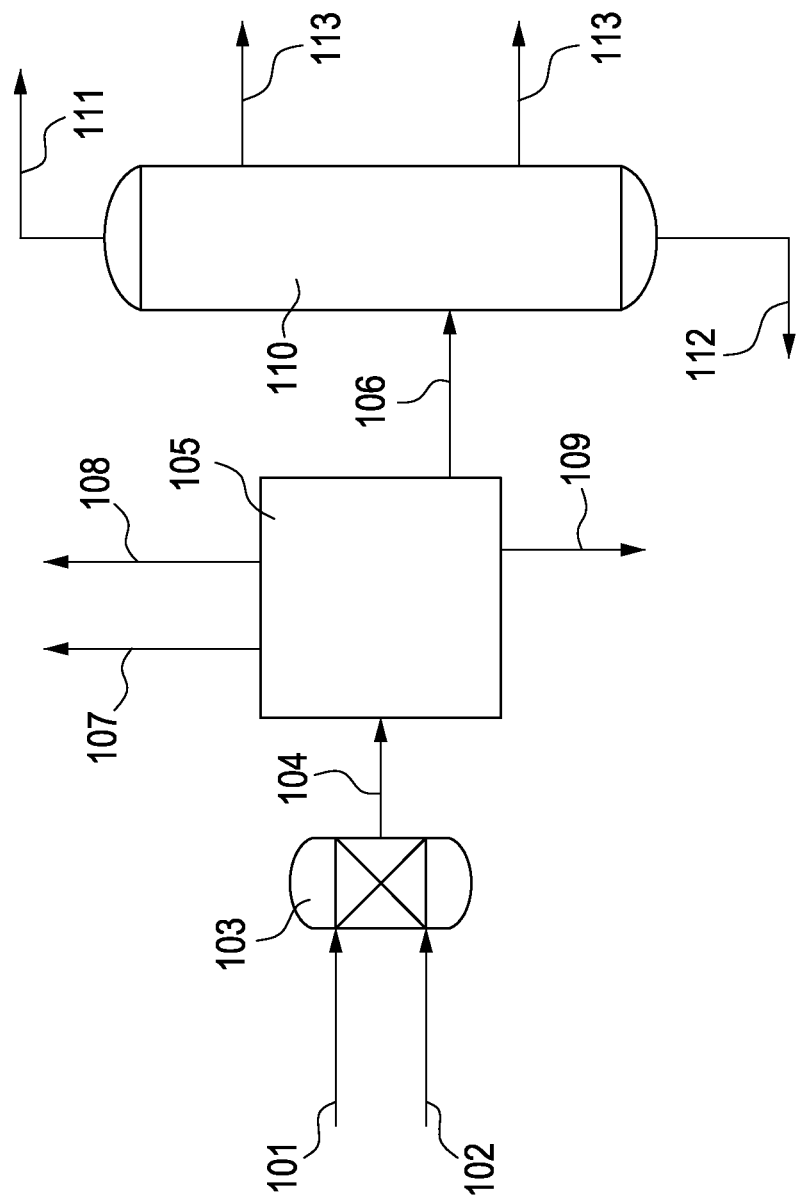
FIG. 1 is a schematic diagram of an exemplary hydrogenation system having a column to remove $C_3+$ alcohols in accordance with one embodiment of the present invention.

FIG. 1 is an exemplary schematic of a system 100 for ethanol production and recovery by acetic acid hydrogenation. Hydrogen 101 and acetic acid 102 are fed to reactor 103 to produce a crude product 104. Crude product 104 is fed to separation section 105 to yield intermediate stream 106 comprising $C_2+$ alcohols (i.e., ethanol and $C_3+$ alcohols) and water. Separation section 105 comprises one or more columns, flashers, membranes, and/or adsorption units. Preferably, intermediate stream 106 is a distillate stream from a column in separation section 105. Separation section 105 may also remove unreacted acid 107 when the conversion is not complete, any organic or light components 108 formed during acetic acid hydrogenation, and/or non-condensable gases 109. Streams 107, 108 and/or 109 may be returned to the reactor 103.

As shown in FIG. 1, in recovering ethanol, embodiments of the present invention separate intermediate stream 106 in distillation column 110. Generally, the water in intermediate stream 106 fed to column 110 is greater than the azeotropic amount of water, e.g., greater than about 4.5 wt. % water. In some embodiments, intermediate stream 106 comprises from 20 to 95 wt. % $C_2+$ alcohols, where of those $C_2+$ alcohols 90% to 99.9% are ethanol and from 0.1% to 10% are $C_3+$ alcohols. In preferred embodiments, the $C_2+$ alcohols composition comprises 95 to 99.9 wt. % ethanol and 0.1 to 5 wt. % $C_3+$ alcohols. The separation of intermediate stream 106 is controlled by thermodynamic phase equilibrium, which provides a concentration gradient throughout column 110 such that ethanol may be withdrawn overhead in distillate stream 111 and water may exit the bottom in residue stream 112. However, when additional species, such as $C_3+$ alcohols, are present in the intermediate stream 106, a concentration gradient sufficient for separation may not exist, thereby causing the $C_3+$ alcohols to build up, e.g., bulge, at particular points within column 110. In addition, these $C_3+$ alcohols may be forced to exit the column 110 with the ethanol in line 111 or water in line 112, thus causing impurities in those streams.

Embodiments of the present invention regulate the $C_3+$ alcohols concentration in the recovered ethanol by taking one or more sidedraws 113 from distillation column 110. Sidedraws 113 may be taken continuously or intermittently as necessary to remove $C_3+$ alcohols. In some embodiments, multiple sidedraws 113 may be taken throughout the column to control the $C_3+$ alcohols concentration in distillate 111 and/or residue 112. Sidedraws 113 of $C_3+$ alcohols may be taken in the liquid or vapor phase. In preferred embodiments, sidedraws 113 are taken at locations in column 110 approximate to where the $C_3+$ alcohols tend to build up.

In one embodiment, sidedraws 113 remove the $C_3+$ alcohols such that distillate stream 111 comprises less than 1000 wppm of $C_3+$ alcohols, e.g., less than 500 wppm or less than 400 wppm. In terms of ranges, the $C_3+$ alcohols concentration range in distillate stream 111 may be from 10 to 1000 wppm, e.g., from 10 to 500 wppm or from 10 to 400 wppm. In particular, the concentration of isopropanol and/or n-propanol in distillate stream 111 may be less than 1000 wppm, e.g., less than 500 wppm or less than 400 wppm.

Sidedraws 113 primarily contain ethanol and/or water, as well as $C_3+$ alcohols. The amount of $C_3+$ alcohols in sidedraws 113 may vary widely. In some embodiments, there may be higher concentrations of the $C_3+$ alcohols in the sidedraws 113 than in either distillate stream 111 or residue stream 112. For example, the concentration of the $C_3+$ alcohols in sidedraws 113 may be greater than 0.05 wt. %, e.g., greater than 0.1 wt. % or greater than 0.5 wt. %. The $C_3+$ alcohols removed via sidedraws 113 are generally purged or discarded. The flow rate of sidedraws 113 may vary and may be dependent upon variables such as, for example, the specification for $C_3+$ alcohols concentration in the ethanol product, size and location of bulging of trays within column 110, and column 110 operation parameters. Additional separation of sidedraws 113 is generally inefficient, but may be performed to recover remaining ethanol and/or water from the $C_3+$ alcohols.

Embodiments of the process of the present invention may regulate the $C_3+$ alcohols concentration in the residue stream 112. In some embodiments, sidedraws 113 remove the $C_3+$ alcohols such that residue stream 112 comprises less than 1000 wppm of $C_3+$ alcohols, e.g., less than 500 wppm or less than 400 wppm. In certain embodiments, the water in the residue stream 112 may be reused in the process for extractive distillation or hydrolysis. Thus, it may be beneficial to withdraw $C_3+$ alcohols that build up in the lower or stripping section of distillation column 110.

Optionally, an analyzer (not shown) may be used to measure the $C_3+$ alcohols concentration in the distillate stream 111 and/or residue stream 112. When the analyzer measures that the concentration of the composition within column 110 exceeds a target or specification level for the particular $C_3+$ alcohols, a signal may be provided and a sidedraw may be taken from column 110 to reduce the $C_3+$ alcohols concentration in the distillate 111 and/or residue stream 112. For example, a target level of $C_3+$ alcohols concentration may be less than 1000 wppm, e.g., less than 500 wppm, or less than 400 wppm. One or more additional analyzers may also be used to measure the $C_3+$ alcohols concentration throughout the column.

The process of the present invention may be used with any ethanol production, preferably with ethanol produced by acetic acid hydrogenation. The materials, catalyst, reaction conditions, and separation are described further below.

The raw materials, acetic acid and hydrogen, used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. As petroleum and natural gas prices fluctuate, becoming either more or less expensive, methods for producing acetic acid and intermediates such as methanol and carbon monoxide from alternate carbon sources have drawn increasing interest. In particular, when petroleum is relatively expensive compared to natural gas, it may become advantageous to produce acetic acid from synthesis gas ("syn gas") that is derived from any available carbon source. U.S. Pat. No. 6,232,352, the disclosure of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syn gas is diverted from the methanol synthesis loop and supplied to a separator unit to recover CO and hydrogen, which are then used to produce acetic acid. In a similar manner, hydrogen for the hydrogenation step may be supplied from syn gas.

In some embodiments, some or all of the raw materials for the above-described acetic acid hydrogenation process may be derived partially or entirely from syngas. For example, the acetic acid may be formed from methanol and carbon monoxide, both of which may be derived from syngas. For example, the methanol may be formed by steam reforming syngas, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof.

Methanol carbonylation processes suitable for production of acetic acid are described in U.S. Pat. Nos. 7,208,624, 7,115,772, 7,005,541, 6,657,078, 6,627,770, 6,143,930, 5,599,976, 5,144,068, 5,026,908, 5,001,259, and 4,994,608, the entire disclosures of which are incorporated herein by reference. Optionally, the production of ethanol may be integrated with such methanol carbonylation processes.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syn gas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

The acetic acid fed to the hydrogenation reactor may also comprise other carboxylic acids and anhydrides, as well as acetaldehyde and acetone. Preferably, a suitable acetic acid feed stream comprises one or more compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

The acetic acid may be vaporized at the reaction temperature, following which the vaporized acetic acid can be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is transferred to the vapor state by passing hydrogen, recycle gas, another suitable gas, or mixtures thereof through the acetic acid at a temperature below the boiling point of acetic acid, thereby humidifying the carrier gas with acetic acid vapors, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

Some embodiments of the process of hydrogenating acetic acid to form ethanol may include a variety of configurations using a fixed bed reactor or a fluidized bed reactor. In many embodiments of the present invention, an "adiabatic" reactor can be used. In these embodiments, there is little or no need for internal plumbing through the reaction zone to add or remove heat. In other embodiments, a radial flow reactor or reactors may be employed, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 KPa to 3000 KPa (about 1.5 to 435 psi), e.g., from 50 KPa to 2300 KPa, or from 100 KPa to 1500 KPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 hr$^{-1}$. In terms of ranges the GHSV may range from 50 hr$^{-1}$ to 50,000 hr$^{-1}$, e.g., from 500 hr$^{-1}$ to 30,000 hr$^{-1}$, from 1000 hr$^{-1}$ to 10,000 hr$^{-1}$, or from 1000 hr$^{-1}$ to 6500 hr$^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 hr$^{-1}$ or 6,500 hr$^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1.

Contact or residence time can also vary widely, depending upon such variables as amount of acetic acid, catalyst, reactor, temperature and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

The hydrogenation of acetic acid to form ethanol is preferably conducted in the presence of a hydrogenation catalyst. Suitable hydrogenation catalysts include catalysts comprising a first metal and optionally one or more of a second metal, a third metal or any number of additional metals, optionally on a catalyst support. The first and optional second and third metals may be selected from Group IB, IIB, IIIB, IVB, VB, VIIB, VIIB, VIII transition metals, a lanthanide metal, an actinide metal, or a metal selected from any of Groups IIIA, IVA, VA, and VIA. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, silver/palladium, copper/palladium, nickel/palladium, gold/palladium, ruthenium/rhenium, and ruthenium/iron. Exemplary catalysts are further described in U.S. Pat. Nos. 7,608,744 and 7,863,489 and U.S. Pub. No. 2010/0197485, the entireties of which are incorporated herein by reference.

In one embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. In embodiments of the invention where the first metal comprises platinum, it is preferred that the catalyst comprises platinum in an amount less than 5 wt. %, e.g., less than 3 wt. % or less than 1 wt. %, due to the high commercial demand for platinum.

As indicated above, in some embodiments, the catalyst further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. Most preferably, the second metal is selected from tin and rhenium.

In certain embodiments where the catalyst includes two or more metals, e.g., a first metal and a second metal, the first metal is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 5 wt. %. For catalysts comprising two or more metals, the two or more metals may be alloyed with one another, or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from both the first and second metals. In preferred embodiments, the third metal is selected from the group consisting of cobalt, palladium, ruthenium, copper, zinc, platinum, tin, and rhenium. More preferably, the third metal is selected from cobalt, palladium, and ruthenium. When present, the total weight of the third metal is preferably from 0.05 to 4 wt. %, e.g., from 0.1 to 3 wt. %, or from 0.1 to 2 wt. %.

In addition to one or more metals, in some embodiments of the present invention, the catalysts further comprise a support or a modified support. As used herein, the term "modified support" refers to a support that includes a support material and a support modifier, which adjusts the acidity of the support material.

The total weight of the support or modified support, based on the total weight of the catalyst, preferably is from 75 to 99.9 wt. %, e.g., from 78 to 97 wt. %, or from 80 to 95 wt. %. In preferred embodiments that utilize a modified support, the support modifier is present in an amount from 0.1 to 50 wt. %, e.g., from 0.2 to 25 wt. %, from 0.5 to 15 wt. %, or from 1 to 8 wt. %, based on the total weight of the catalyst. The metals of the catalysts may be dispersed throughout the support, layered throughout the support, coated on the outer surface of the support (i.e., egg shell), or decorated on the surface of the support.

As will be appreciated by those of ordinary skill in the art, support materials are selected such that the catalyst system is suitably active, selective and robust under the process conditions employed for the formation of ethanol.

Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

As indicated, the catalyst support may be modified with a support modifier. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include $WO_3$, $MoO_3$, $Fe_2O_3$, $Cr_2O_3$, $V_2O_5$, $MnO_2$, $CuO$, $Co_2O_3$, and $Bi_2O_3$.

In another embodiment, the support modifier may be a basic modifier that has a low volatility or no volatility. Such basic modifiers, for example, may be selected from the group consisting of: (i) alkaline earth oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. The basic support modifier may be selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$). If the basic support modifier comprises calcium metasilicate, it is preferred that at least a portion of the calcium metasilicate is in crystalline form.

A preferred silica support material is SS61138 High Surface Area (HSA) Silica Catalyst Carrier from Saint Gobain NorPro. The Saint-Gobain NorPro SS61138 silica exhibits the following properties: contains approximately 95 wt. % high surface area silica; surface area of about 250 $m^2/g$; median pore diameter of about 12 nm; average pore volume of about 1.0 $cm^3/g$ as measured by mercury intrusion porosimetry; and packing density of about 0.352 $g/cm^3$ (22 $lb/ft^3$).

Another preferred silica support material is KA-160 silica spheres from Süd-Chemie having a nominal diameter of about 5 mm, a density of about 0.562 g/ml, an absorptivity of about 0.583 g $H_2O$/g support, a surface area of about 160 to 175 $m^2/g$, and a pore volume of about 0.68 ml/g.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197485 referred to above, the entireties of which are incorporated herein by reference.

In particular, the hydrogenation of acetic acid may achieve favorable conversion of acetic acid and favorable selectivity and productivity to ethanol. For purposes of the present invention, the term "conversion" refers to the amount of acetic acid in the feed that is converted to a compound other than acetic acid. Conversion is expressed as a mole percentage based on acetic acid in the feed. The conversion may be at least 10%, e.g., at least 20%, at least 40%, at least 50%, at least 60%, at least 70% or at least 80%. Although catalysts that have high conversions are desirable, such as at least 80% or at least 90%, in some embodiments, a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. Preferably, the catalyst selectivity to ethoxylates is at least 60%, e.g., at least 70%, or at least 80%. As used herein, the term "ethoxylates" refers specifically to the compounds ethanol, acetaldehyde, and ethyl acetate. Preferably, the selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 200 grams of ethanol per kilogram catalyst per hour, e.g., at least 400 grams of ethanol per kilogram catalyst per hour, or at least 600 grams of ethanol per kilogram catalyst per hour, is preferred. In terms of ranges, the productivity preferably is from 200 to 3,000 grams of ethanol per kilogram catalyst per hour, e.g., from 400 to 2,500 grams of ethanol per kilogram catalyst per hour or from 600 to 2,000 grams of ethanol per kilogram catalyst per hour.

Operating under the conditions of the present invention may result in ethanol production on the order of at least 0.1 tons of ethanol per hour, e.g., at least 1 ton of ethanol per hour, at least 5 tons of ethanol per hour, or at least 10 tons of ethanol per hour. Larger scale industrial production of ethanol, depending on the scale, generally should be at least 15 tons of ethanol per hour, preferably at least 30 tons of ethanol per hour. In terms of ranges, for large scale industrial production of ethanol, the process of the present invention may produce 15 to 160 tons of ethanol per hour, e.g., 30 to 80 tons of ethanol per hour. Ethanol production from fermentation, due the economies of scale, typically does not permit the single facility ethanol production that may be achievable by employing embodiments of the present invention.

In various embodiments of the present invention, the crude ethanol product produced by the hydrogenation process, before any subsequent processing, such as purification and separation, will typically comprise unreacted acetic acid, ethanol and water. As used herein, the term "crude ethanol product" refers to any composition comprising from 5 to 70 wt. % ethanol and from 5 to 35 wt. % water. In some exemplary embodiments, the crude ethanol product comprises ethanol in an amount from 5 to 70 wt. %, e.g., from 10 to 60 wt. %, or from 15 to 50 wt. %, based on the total weight of the crude ethanol product. Preferably, the crude ethanol product contains at least 10 wt. % ethanol, at least 15 wt. % ethanol or at least 20 wt. % ethanol. The crude ethanol product typically will further comprise unreacted acetic acid, depending on conversion, for example, in an amount of less than 90 wt. %, e.g., less than 80 wt. % or less than 70 wt. %. In terms of ranges, the unreacted acetic acid optionally is present in the crude ethanol product in an amount from 0 to 90 wt. %, e.g., from 5 to 80 wt. %, from 15 to 70 wt. %, from 20 to 70 wt. % or from 25 to 65 wt. %. As water is formed in the reaction process, water will generally be present in the crude ethanol product, for example, in amounts ranging from 5 to 35 wt. %, e.g., from 10 to 30 wt. % or from 10 to 26 wt. %.

In addition to ethanol, acetic acid, and water, the crude product may comprise $C_3$+ alcohols that form from impurities, such as propanoic acid. These $C_3$+ alcohols may be present, for example, in amounts of less than about 8 wt. %, and generally less than 1 wt. % and more preferably less than 0.5 wt. %. Without being bound by theory, the low levels of $C_3$+ alcohols concentration in the crude product increases the demand for an effective process for the separation of the $C_3$+ alcohols.

Ethyl acetate may also be produced during the hydrogenation of acetic acid, or through side reactions and may be present, for example, in amounts ranging from 0 to 20 wt. %, e.g., from 0 to 15 wt. %, from 1 to 12 wt. % or from 3 to 10 wt. %. In addition, acetaldehyde may be produced through side reactions, and may be present, for example, in amounts ranging from 0 to 10 wt. %, e.g., from 0 to 3 wt. %, from 0.1 to 3 wt. % or from 0.2 to 2 wt. %. Other components, such as, for example, esters, ethers, aldehydes, ketones, alkanes, and carbon dioxide, if detectable, collectively may be present in amounts less than 10 wt. %, e.g., less than 6 wt. % or less than 4 wt. %. In terms of ranges, these other components may be collectively present in an amount from 0.1 to 10 wt. %, e.g., from 0.1 to 6 wt. %, or from 0.1 to 4 wt. %. Exemplary component ranges for the crude ethanol product are provided in Table 1.

TABLE 1

CRUDE ETHANOL PRODUCT

| Component | Conc. (wt. %) | Conc. (wt. %) | Conc. (wt. %) | Conc. (wt. %) |
|---|---|---|---|---|
| Ethanol | 5 to 70 | 10 to 60 | 15 to 50 | 25 to 50 |
| Acetic Acid | 0 to 90 | 5 to 80 | 15 to 70 | 20 to 70 |
| Water | 5 to 35 | 5 to 30 | 10 to 30 | 10 to 26 |
| Ethyl Acetate | 0 to 20 | 0 to 15 | 1 to 12 | 3 to 10 |
| Acetaldehyde | 0 to 10 | 0 to 3 | 0.1 to 3 | 0.2 to 2 |
| $C_3+$ Alcohols | 0.0001 to 8 | 0.0001 to 0.1 | 0.0001 to 0.05 | — |
| Others | 0.1 to 10 | 0.1 to 6 | 0.1 to 4 | — |

Figure 2:
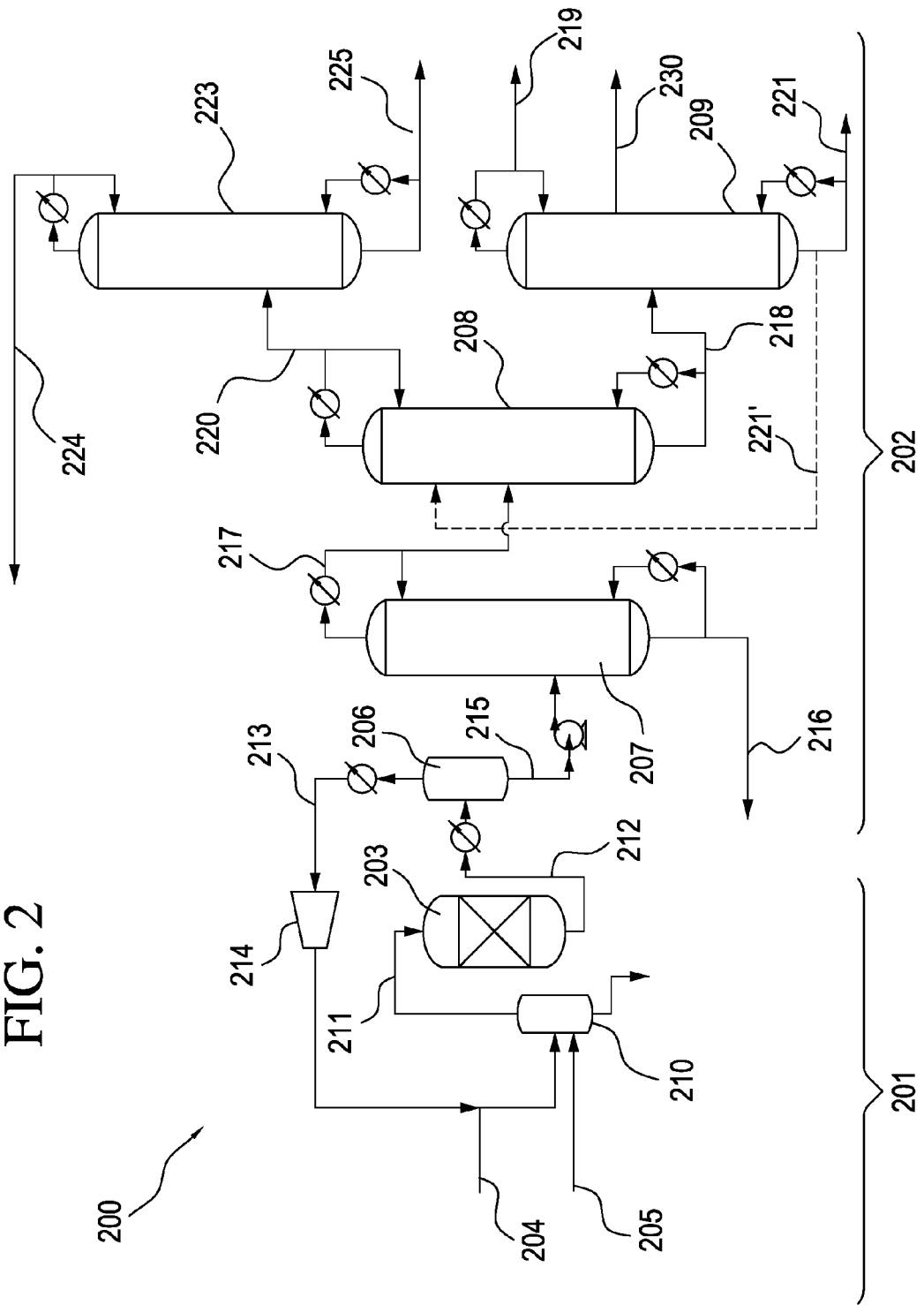
FIG. 2 is a schematic diagram of an exemplary hydrogenation system in accordance with another embodiment of the present invention.

The crude ethanol product containing $C_3+$ alcohols may be treated to control the amount of $C_3+$ alcohols in the ethanol product, as shown by an exemplary hydrogenation system 200 in FIG. 2. System 200 comprises reaction zone 201 and distillation zone 202. Reaction zone 201 comprises reactor 203, hydrogen feed line 204 and acetic acid feed line 205. Distillation zone 202 comprises flasher 206, first column 207, second column 208, third column 209, and fourth column 223. Hydrogen and acetic acid are fed to a vaporizer 210 via lines 204 and 205, respectively, to create a vapor feed stream in line 211 that is directed to reactor 203. In one embodiment, lines 204 and 205 may be combined and jointly fed to the vaporizer 210, e.g., in one stream containing both hydrogen and acetic acid. The temperature of the vapor feed stream in line 211 is preferably from 100° C. to 350° C., e.g., from 120° C. to 310° C. or from 150° C. to 300° C. Any feed that is not vaporized is removed from vaporizer 210, as shown in FIG. 2, and may be recycled thereto. In addition, although FIG. 2 shows line 211 being directed to the top of reactor 203, line 211 may be directed to the side, upper portion, or bottom of reactor 203. Further modifications and additional components to reaction zone 201 are described below.

Reactor 203 contains the catalyst that is used in the hydrogenation of the carboxylic acid, preferably acetic acid. In one embodiment, one or more guard beds (not shown) may be used to protect the catalyst from poisons or undesirable impurities contained in the feed or return/recycle streams. Such guard beds may be employed in the vapor or liquid streams. Suitable guard bed materials are known in the art and include, for example, carbon, silica, alumina, ceramic, or resins. In certain embodiments of the invention, the guard bed media is functionalized to trap particular species such as sulfur or halogens. During the hydrogenation process, a crude ethanol product is withdrawn, preferably continuously, from reactor 203 via line 212.

The crude ethanol product may be condensed and fed to flasher 206, which, in turn, provides a vapor stream and a liquid stream. The flasher 206 may operate at a temperature of from 50° C. to 500° C., e.g., from 70° C. to 400° C. or from 100° C. to 350° C. The pressure of flasher 206 may be from 50 KPa to 2000 KPa, e.g., from 75 KPa to 1500 KPa or from 100 to 1000 KPa. In another embodiment, the temperature and pressure of the flasher is similar to the temperature and pressure of the reactor 203.

The vapor stream exiting the flasher 206 may comprise hydrogen and hydrocarbons, which may be purged and/or returned to reaction zone 201 via line 213. As shown in FIG. 2, the returned portion of the vapor stream passes through compressor 214 and is combined with the hydrogen feed and co-fed to vaporizer 210.

The liquid from flasher 206 is withdrawn and pumped as a feed composition via line 215 to the side of first column 207, also referred to as an "acid separation column" The contents of line 215 typically will be substantially similar to the product obtained directly from the reactor 203, and may, in fact, also be characterized as a crude ethanol product. However, the feed composition in line 215 preferably has substantially no hydrogen, carbon dioxide, methane or ethane, which are removed by flasher 206. Exemplary compositions of line 215 are provided in Table 2. It should be understood that liquid line 215 may contain other components, not listed, such as additional components in the feed.

TABLE 2

FEED COMPOSITION

| | Conc. (wt. %) | Conc. (wt. %) | Conc. (wt. %) |
|---|---|---|---|
| Ethanol | 5 to 70 | 10 to 60 | 15 to 50 |
| Acetic Acid | <90 | 5 to 80 | 15 to 70 |
| Water | 5 to 35 | 5 to 30 | 10 to 30 |
| Ethyl Acetate | <20 | 0.001 to 15 | 1 to 12 |
| Acetaldehyde | <10 | 0.001 to 3 | 0.1 to 3 |
| Acetal | <5 | 0.001 to 2 | 0.005 to 1 |
| Acetone | <5 | 0.0005 to 0.05 | 0.001 to 0.03 |
| $C_3+$ Alcohols | <8 | <0.1 | <0.05 |
| Other Esters | <5 | <0.005 | <0.001 |
| Other Ethers | <5 | <0.005 | <0.001 |

The amounts indicated as less than (<) in the tables throughout present application are preferably not present and if present may be present in trace amounts or in amounts greater than 0.0001 wt. %.

The "other esters" in Table 2 may include, but are not limited to, ethyl propionate, methyl acetate, isopropyl acetate, n-propyl acetate, n-butyl acetate or mixtures thereof. The "other ethers" in Table 2 may include, but are not limited to, diethyl ether, methyl ethyl ether, isobutyl ethyl ether or mixtures thereof. It should be understood that these other components may be carried through in any of the distillate or residue streams described herein.

Optionally, the crude ethanol product may pass through one or more membranes to separate hydrogen and/or other non-condensable gases. In other optional embodiments, the crude ethanol product may be fed directly to the acid separation column as a vapor feed and the non-condensable gases may be recovered from the overhead of the column.

When the content of acetic acid in line 215 is less than 5 wt. %, the acid separation column 207 may be skipped and line 215 may be introduced directly to second column 208, also referred to herein as a "light ends column."

In the embodiment shown in FIG. 2, line 215 is introduced in the lower part of first column 207, e.g., lower half or lower third. Depending on the acetic acid conversion and operation of column 207, unreacted acetic acid, water, and other heavy components, if present, are removed from the composition in line 215 and are withdrawn, preferably continuously, as residue. In some embodiments, especially with higher conversions of acetic acid of at least 80%, or at least 90%, it may be beneficial to remove a majority of water in line 215 along with substantially all the acetic acid in residue stream 216. Residue stream 216 may be recycled to reaction zone 201. In addition, a portion of the water in residue stream 216 may be separated and purged with the acid rich portion being returned to reaction zone 201. In other embodiments, the residue stream 216 may be a dilute acid stream that may be treated in a weak acid recovery system or sent to a reactive distillation column to convert the acid to esters.

First column 207 also forms an overhead distillate, which is withdrawn in line 217, and which may be condensed and refluxed, for example, at a ratio of from 10:1 to 1:10, e.g., from 3:1 to 1:3 or from 1:2 to 2:1.

Any of columns 207, 208, 209, or 223 may comprise any distillation column capable of performing the desired separation and/or purification. Each of the columns preferably comprises a tray column having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section and so on.

The associated condensers and liquid separation vessels that may be employed with each of the distillation columns may be of any conventional design and are simplified in FIG. 2. As shown in FIG. 2, heat may be supplied to the base of each column or to a circulating bottom stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and one flasher are shown in FIG. 2, additional reactors, flashers, condensers, heating elements, and other components may be used in various embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in the columns may vary. As a practical matter, pressures from 10 KPa to 3000 KPa will generally be employed in these zones although in some embodiments subatmospheric pressures or superatmospheric pressures may be employed. Temperatures within the various zones will normally range between the boiling points of the composition removed as the distillate and the composition removed as the residue. As will be recognized by those skilled in the art, the temperature at a given location in an operating distillation column is dependent on the composition of the material at that location and the pressure of column. In addition, feed rates may vary depending on the size of the production process and, if described, may be generically referred to in terms of feed weight ratios.

When column 207 is operated under standard atmospheric pressure, the temperature of the residue exiting in line 216 from column 207 preferably is from 95° C. to 120° C., e.g., from 105° C. to 117° C. or from 110° C. to 115° C. The temperature of the distillate exiting in line 217 from column 207 preferably is from 70° C. to 110° C., e.g., from 75° C. to 95° C. or from 80° C. to 90° C. In other embodiments, the pressure of first column 207 may range from 0.1 KPa to 510 KPa, e.g., from 1 KPa to 475 KPa or from 1 KPa to 375 KPa. Distillate and residue compositions for first column 207 for one exemplary embodiment of the present invention are provided in Table 3. Note that these compositions may change depending on acetic acid conversion, the operation of the column, and whether a majority of the water is removed in the residue. For purposes of the present invention, the $C_3+$ alcohols pass along with ethanol in the distillate stream 217. In addition, for convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

TABLE 3

| FIRST COLUMN | | | |
|---|---|---|---|
| | Conc. (wt. %) | Conc. (wt. %) | Conc. (wt. %) |
| Distillate | | | |
| Ethanol | 20 to 75 | 30 to 70 | 40 to 65 |
| Water | 10 to 40 | 15 to 35 | 20 to 35 |
| Acetic Acid | <2 | 0.001 to 0.5 | 0.01 to 0.2 |
| Ethyl Acetate | <60 | 5.0 to 40 | 10 to 30 |
| Acetaldehyde | <10 | 0.001 to 5 | 0.01 to 4 |
| Acetal | <0.1 | <0.1 | <0.05 |
| Acetone | <0.05 | 0.001 to 0.03 | 0.01 to 0.025 |
| $C_3+$ Alcohols | <8 | <0.1 | <0.05 |
| Residue | | | |
| Acetic Acid | 60 to 100 | 70 to 95 | 85 to 92 |
| Water | <30 | 1 to 20 | 1 to 15 |
| Ethanol | <1 | <0.9 | <0.07 |

Some species, such as acetals, may decompose in column 207 to low or even undetectable amounts. In addition, there may be a non-catalyzed equilibrium reaction after the crude ethanol product 212 exits the reactor 203 in liquid feed 215. Depending on the concentration of acetic acid, equilibrium may be driven towards formation of ethyl acetate. The equilibrium may be regulated using the residence time and/or temperature of liquid feed 215.

The distillate, e.g., overhead stream, of column 207 optionally is condensed and refluxed as shown in FIG. 2, preferably, at a reflux ratio of 1:5 to 10:1. The distillate in line 217 preferably comprises ethanol, ethyl acetate, water, and $C_3+$ alcohols. The separation of these species may be difficult, in some cases, due to the formation of binary and tertiary azeotropes.

The first distillate in line 217 is introduced to the second column 208, also referred to as a "light ends column," preferably in the middle part of column 208, e.g., middle half or middle third. The $C_3+$ alcohols concentrate with the ethanol in the bottom of column 208. Second column 208 may be a tray column or packed column. In one embodiment, second column 208 is a tray column having from 5 to 70 trays, e.g., from 15 to 50 trays, or from 20 to 45 trays. As one example, when a 25 tray column is used in a column without water extraction, line 217 is introduced at tray 17. In another embodiment, the second column 208 may be an extractive distillation column. In such an embodiment, an extraction agent, such as water, may be added to second column 208. If the extraction agent comprises water, it may be obtained from an external source or from an internal return/recycle line from one or more of the other columns.

In some embodiments, a portion of the water in first distillate 217 may be removed prior to second column 208, using one or more membranes, and/or adsorptions units.

Although the temperature and pressure of second column 208 may vary, when second column 208 is operating at atmospheric pressure, the temperature of the second residue exiting in line 218 from second column 208 preferably is from 60° C. to 90° C., e.g., from 70° C. to 90° C. or from 80° C. to 90° C. The temperature of the second distillate exiting in line 220 from second column 208 preferably is from 50° C. to 90° C., e.g., from 60° C. to 80° C. or from 60° C. to 70° C. In other embodiments, the pressure of second column 208 may range from 0.1 KPa to 510 KPa, e.g., from 1 KPa to 475 KPa or from 1 KPa to 375 KPa. Exemplary distillate and residue compositions for second column 208 are provided in Table 4 below. It should be understood that the distillate and residue may also contain other components, not listed, such as additional components in the feed.

TABLE 4

SECOND COLUMN

|  | Conc. (wt. %) | Conc. (wt. %) | Conc. (wt. %) |
|---|---|---|---|
| Distillate |  |  |  |
| Ethyl Acetate | 10 to 90 | 25 to 90 | 50 to 90 |
| Acetaldehyde | 1 to 25 | 1 to 15 | 1 to 8 |
| Water | 1 to 25 | 1 to 20 | 4 to 16 |
| Ethanol | <30 | 0.001 to 15 | 0.01 to 5 |
| Acetal | <5 | 0.001 to 2 | 0.01 to 1 |
| Residue |  |  |  |
| Water | 5 to 70 | 30 to 60 | 30 to 50 |
| Ethanol | 20 to 95 | 30 to 70 | 40 to 70 |
| Ethyl Acetate | <3 | 0.001 to 2 | 0.001 to 0.5 |
| Acetic Acid | <0.5 | 0.001 to 0.3 | 0.001 to 0.2 |
| $C_3+$ Alcohols | <8 | <1 | <0.05 |

The weight ratio of ethanol in the second residue to ethanol in the second distillate preferably is at least 3:1, e.g., at least 6:1, at least 8:1, at least 10:1 or at least 15:1. The weight ratio of ethyl acetate in the second residue to ethyl acetate in the second distillate preferably is less than 0.4:1, e.g., less than 0.2:1 or less than 0.1:1. In embodiments that use an extractive column with water as an extraction agent as the second column 208, the weight ratio of ethyl acetate in the second residue to ethyl acetate in the second distillate approaches zero.

Returning to the second distillate, which comprises ethyl acetate and/or acetaldehyde, the second distillate preferably is refluxed as shown in FIG. 2, for example, at a reflux ratio of from 1:10 to 10:1, e.g., from 1:5 to 5:1 or from 1:3 to 3:1. In some embodiments, the second distillate in line 220 or portion thereof may be returned to reactor 203. For example, it may be advantageous to return a portion of second distillate 220 to reactor 203 when no acetic acid is returned via first residue 216 to reactor 203. In certain embodiments and as shown in FIG. 2, the second distillate may be fed to fourth column 223, also referred to as an "acetaldehyde removal column" to recover aldehyde that may be recycled to the reactor 203. In particular, in fourth column 223, the second distillate is separated into a fourth distillate, which comprises acetaldehyde, in line 224 and a fourth residue, which comprises ethyl acetate, in line 225. In these embodiments, the fourth distillate preferably is refluxed at a reflux ratio of from 1:20 to 20:1, e.g., from 1:15 to 15:1 or from 1:10 to 10:1. In other embodiments, the second distillate may be hydrolyzed or fed to a hydrogenolysis reactor (not shown) to produce ethanol from ethyl acetate. In still other embodiments, the second distillate may be purged from system.

As shown in FIG. 2, the second residue from the bottom of second column 208, which comprises ethanol and water, is fed via line 218 to third column 209, also referred to as a "product column." The second residue in line 218 is introduced in the lower part of third column 209, e.g., lower half or lower third. Third column 209 is equipped with one or more sidedraws 230 to separate $C_3+$ alcohols that build up throughout column 209. Third column 209 recovers ethanol as the distillate in line 219 and controls the $C_3+$ alcohols concentration in distillate 219 using sidedraw 230. The distillate 219 of third column 209 preferably is refluxed, for example, at a reflux ratio of from 1:10 to 10:1, e.g., from 1:3 to 3:1 or from 1:2 to 2:1.

In preferred embodiments, the $C_3+$ alcohols concentration in distillate 219 is optimized using sidedraw 230 to be within operating limits, but in some embodiments it may be desirable to remove substantially all of the $C_3+$ alcohols from distillate 219.

Although only one sidedraw stream 230 is depicted in FIG. 2, in accordance with various embodiments of the present invention, a plurality of sidedraws may remove $C_3+$ alcohols from column 209. As indicated above, the composition of a particular sidedraw depends on where the species of the $C_3+$ alcohols build up in column 209. The concentration of $C_3+$ alcohols in a sidedraw may vary as necessary to control the $C_3+$ alcohols concentration in distillate and/or residue of column 209. For example, in some embodiments, a sidedraw may comprise up to 99 wt. % ethanol and/or water, e.g., up to 95 wt. % or up to 90 wt. %, and less than 10 wt. % $C_3+$ alcohols, e.g., less than 5 wt. % or less than 1 wt. %.

In preferred embodiments, the third residue in line 221, which preferably comprises primarily water, is removed from the system 200. Optionally, the third residue 221 may be partially returned to any portion of the system 200. For example, as shown in FIG. 2, a portion of the third residue in line 221 may be taken via line 221' and returned to second column 208. Various embodiments of the present invention may control the $C_3+$ alcohols concentration in residue 221 using sidedraw 230.

Third column 209 is preferably a tray column as described above and preferably operates at atmospheric pressure. The temperature of the third distillate exiting in line 219 from third column 209 preferably is from 60° C. to 110° C., e.g., from 70° C. to 100° C. or from 75° C. to 95° C. The temperature of the third residue exiting from third column 209 in line

221 preferably is from 70° C. to 115° C., e.g., from 80° C. to 110° C. or from 85° C. to 105° C., when column 209 is operated at atmospheric pressure. Exemplary distillate compositions and residue compositions for third column 109 are provided in Table 5 below.

TABLE 5

THIRD COLUMN

|  | Conc. (wt. %) | Conc. (wt. %) | Conc. (wt. %) |
|---|---|---|---|
| Distillate |  |  |  |
| Ethanol | 75 to 96 | 80 to 96 | 85 to 96 |
| Water | <12 | 1 to 9 | 3 to 8 |
| Acetic Acid | <1 | 0.001 to 0.1 | 0.005 to 0.01 |
| Ethyl Acetate | <5 | 0.001 to 4 | 0.01 to 3 |
| $C_3+$ Alcohols | <1 | <0.5 | <0.4 |
| Residue |  |  |  |
| Water | 75 to 100 | 80 to 100 | 90 to 100 |
| Ethanol | <0.8 | 0.001 to 0.5 | 0.005 to 0.05 |
| Ethyl Acetate | <1 | 0.001 to 0.5 | 0.005 to 0.2 |
| Acetic Acid | <2 | 0.001 to 0.5 | 0.005 to 0.2 |

Any of the compounds that are carried through the distillation process from the feed or crude reaction product generally remain in the third distillate in amounts of less 0.1 wt. %, based on the total weight of the third distillate composition, e.g., less than 0.05 wt. % or less than 0.02 wt. %. In preferred embodiments, the finished ethanol composition from distillate 219 is substantially free of acetaldehyde and may comprise less than 8 wppm of acetaldehyde, e.g., less than 5 wppm or less than 1 wppm.

In accordance with various embodiments of the present invention, the $C_3+$ alcohols concentration in the finished ethanol composition is controlled within the limits for the particular application of the finished ethanol. In certain embodiments, the finished ethanol comprises less than 1000 wppm of $C_3+$ alcohols, e.g., less than 500 wppm or less than 400 wppm. For example, the amount of isopropanol in the finished ethanol may be from 80 to 1,000 wppm, e.g., from 95 to 1,000 wppm, from 100 to 700 wppm, or from 150 to 500 wppm. In particular, one or more sidedraws 230 may reduce isopropanol concentrations in distillate 219 that exceed 1000 wppm. In preferred embodiments, one or more sidedraws are positioned at a point(s) approximate to where isopropanol builds up in column 209.

Third distillate 219 may be further purified to form an anhydrous ethanol product stream, i.e., "finished anhydrous ethanol," using one or more additional separation systems, such as, for example, distillation columns (e.g., a finishing column), membranes, adsorption units, or molecular sieves. Anhydrous ethanol may be suitable for fuel applications.

The ethanol product may be an industrial grade ethanol comprising from 75 to 96 wt. % ethanol, e.g., from 80 to 96 wt. % or from 85 to 96 wt. % ethanol, based on the total weight of the ethanol product. Exemplary finished ethanol compositional ranges are provided below in Table 6.

TABLE 6

FINISHED ETHANOL

| Component | Conc. (wt. %) | Conc. (wt. %) | Conc. (wt. %) |
|---|---|---|---|
| Ethanol | 75 to 96 | 80 to 96 | 85 to 96 |
| Water | <12 | 1 to 9 | 3 to 8 |
| Acetic Acid | <1 | <0.1 | <0.01 |
| Ethyl Acetate | <2 | <0.5 | <0.05 |

TABLE 6-continued

FINISHED ETHANOL

| Component | Conc. (wt. %) | Conc. (wt. %) | Conc. (wt. %) |
|---|---|---|---|
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition produced by the embodiments of the present invention may be used in a variety of applications including application as fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid. In another application, the finished ethanol composition may be dehydrated to produce ethylene. Any known dehydration catalyst can be employed to dehydrate ethanol, such as those described in copending U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated herein by reference.

EXAMPLES

The following examples describe the various distillation processes of the present invention.

Example 1

A feed composition, as shown in Table 7, was fed to a distillation column. When operating with no sidedraws, the isopropanol and n-propanol concentrated in the distillate.

TABLE 7

FEED COMPOSITION AND DISTILLATION COLUMN

|  |  | Distillation Column | |
|---|---|---|---|
| Component | Feed (wt. %) | Distillate (wt. %) | Residue (wt. %) |
| Ethanol | 35.5 | 90.2 | 0.002 |
| Water | 65.9 | 8.7 | 99.7 |
| Isopropanol | 0.003 | 0.01 | — |
| n-propanol | 0.003 | 0.01 | — |

Samples of the composition were taken from different trays within the column. As shown in Table 8, the concentrations of isopropanol and n-propanol were higher within the distillation column than in the distillate or residue.

TABLE 8

DISTILLATION COLUMN TRAYS

| Tray Location | Distillation Column | |
|---|---|---|
| | isopropanol (wt. %) | n-propanol (wt. %) |
| Distillate | 0.0099 | 0.0101 |
| Tray 40 | 0.0117 | 0.1316 |
| Tray 35 | 0.0104 | 0.3259 |
| Tray 15 | 0 | 0.0005 |
| Residue | 0 | 0 |
| Feed | 0.0024 | 0.0036 |

In particular, Table 8 provides elevated concentrations of both isopropanol and n-propanol on trays 40 and 35, respectively. Visual inspection indicated that liquid mass appeared to be bulging on trays located in the middle of the column.

Example 2

Figure 3:
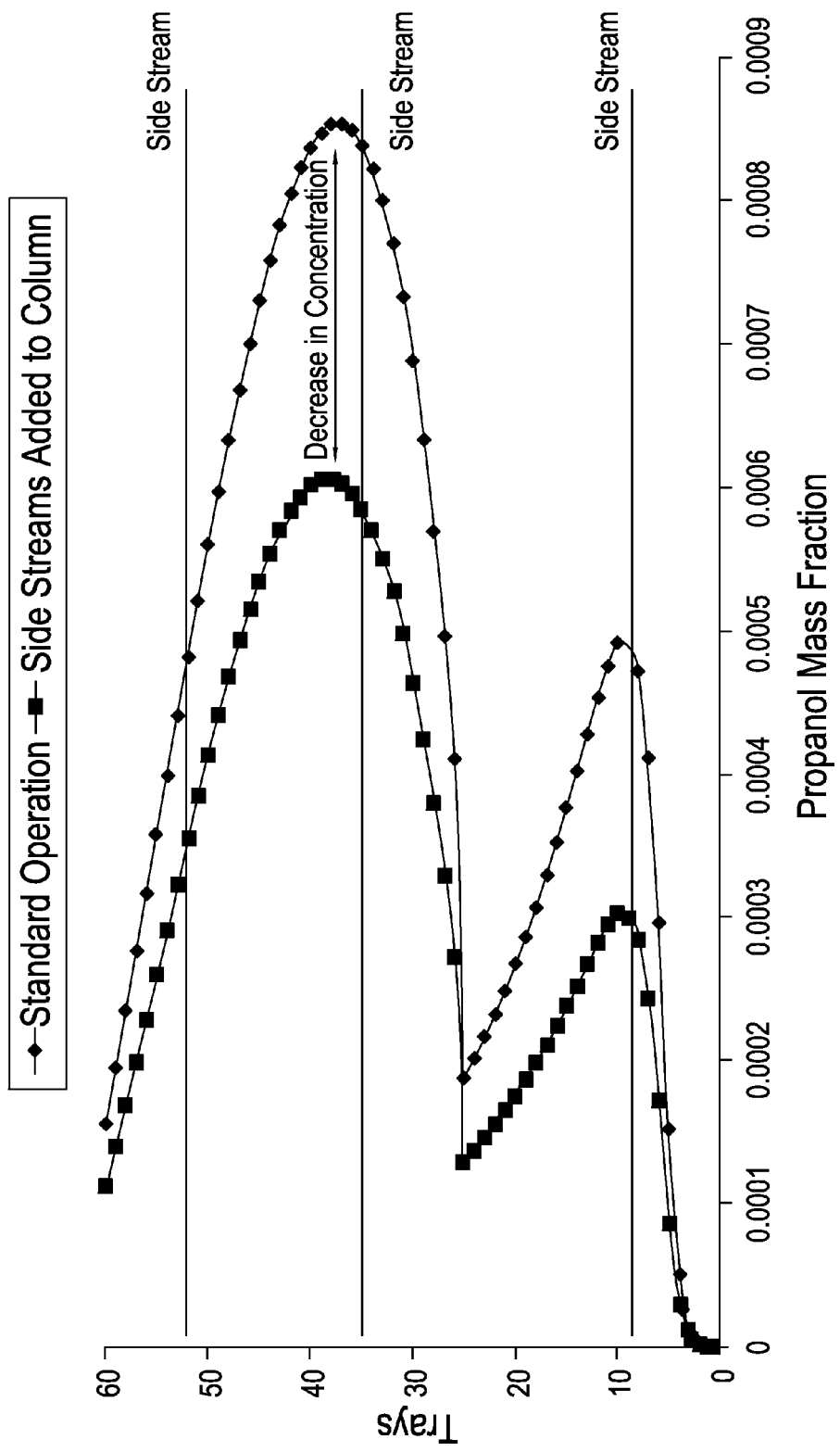
FIG. 3 is a graphical simulation illustrating the reduction of $C_2+$ alcohols bulging as a result of the addition of sidedraws in accordance with one embodiment of the present invention.

Using the feed from Example 1 in Table 7, a distillation column was modeled using Aspen simulation to determine the propanol (specifically the isopropanol and n-propanol) concentration at different locations within the column. Liquid phase sidedraws were simultaneously taken from the column at three locations. Table 9 summarizes the sidedraw compositions and FIG. 3 demonstrates the bulging of propanol within the column.

TABLE 9

SIDEDRAW COMPOSITION

| Tray | Propanol (wt. %) | Ethanol (wt. %) | Water (wt. %) | Phase |
|---|---|---|---|---|
| 54 | 0.029 | 89.1 | 10.9 | Liquid |
| 36 | 0.0602 | 81.1 | 18.9 | Liquid |
| 9 | 0.0294 | 41.6 | 58.3 | Liquid |

By removing isopropanol and n-propanol within the column, the distillate of the column contains 26.1% less propanol than when no sidedraws are taken.

While the invention has been described in detail, modifications within the spirit and scope of the invention will be readily apparent to those of skill in the art. In addition, it should be understood that aspects of the invention and portions of various embodiments and various features recited herein and/or in the appended claims may be combined or interchanged either in whole or in part. In the foregoing descriptions of the various embodiments, those embodiments which refer to another embodiment may be appropriately combined with one or more other embodiments, as will be appreciated by one of skill in the art. Furthermore, those of ordinary skill in the art will appreciate that the foregoing description is by way of example only, and is not intended to limit the invention.

The invention claimed is:

1. A process for recovering ethanol, comprising:
hydrogenating acetic acid in an acetic acid feed stream in the presence of a catalyst to form a crude product;
separating at least a portion of the crude product into an intermediate stream comprising one or more $C_{2+}$ alcohols, and a residue comprising acetic acid; and
separating at least a portion of the intermediate stream in a column into a product distillate comprising ethanol, and one or more sidedraws comprising one or more $C_{3+}$ alcohols.

2. The process of claim 1, wherein said one or more $C_{2+}$ alcohols are selected from the group consisting of ethanol, isopropanol, n-propanol, n-butanol, 2-butanol, isobutanol, tert-butanol, 2,2-dimethyl-1-propanol, 3-pentanol, 2-pentanol, 1-pentanol, 3-methyl-2-butanol, 2-methyl-2-butanol, a mixture thereof, and an azeotrope thereof.

3. The process of claim 1, wherein said one or more sidedraws comprise one or more $C_3$ to $C_6$ alcohols, a mixture thereof, and an azeotrope thereof.

4. The process of claim 1, wherein said one or more $C_{3+}$ alcohols are selected from the group consisting of isopropanol, n-propanol, n-butanol, 2-butanol, isobutanol, tert-butanol, 2,2-dimethyl-1-propanol, 3-pentanol, 2-pentanol, 1-pentanol, 3-methyl-2-butanol, 2-methyl-2-butanol, a mixture thereof, and an azeotrope thereof.

5. The process of claim 1, wherein said intermediate stream comprises said one or more $C_{2+}$ alcohols in an amount from 20 to 95 wt. % and, wherein said one or more $C_{2+}$ alcohols comprises from 90 to 99.9 wt. % ethanol and from 0.001 to 10 wt. % of said one or more $C_{3+}$ alcohols.

6. The process of claim 1, wherein said intermediate stream comprises said one or more $C_{2+}$ alcohols in an amount from 20 to 95 wt. % and, wherein said one or more $C_{2+}$ alcohols comprises from 90 to 99.9 wt. % ethanol and from 0.001 to 10 wt. % of said one or more $C_{3+}$ alcohols.

7. The process of claim 1, wherein said one or more sidedraws are in the liquid phase.

8. The process of claim 1, wherein said one or more sidedraws are in the vapor phase.

9. The process of claim 1, wherein the product distillate comprises substantially none of said one or more $C_{3+}$ alcohols.

10. The process of claim 1, wherein the product distillate comprises less than 1000 wppm of said one of more $C_{3+}$ alcohols.

11. The process of claim 1, further comprising removing a residue comprising water from the at least a portion of the intermediate stream.

12. The process of claim 11, wherein the residue comprises less than 1000 wppm of said one of more $C_{3+}$ alcohols.

13. The process of claim 1, further comprising measuring $C_{3+}$ alcohols concentration in the product distillate and withdrawing said one or more sidedraws when the measured $C_{3+}$ alcohols concentration exceeds a target level.

14. The process of claim 1, wherein the acetic acid feed stream comprises propanoic acid.

15. The process of claim 1, wherein the catalyst comprises a combination of metals selected from the group consisting of platinum/tin, platinum/ruthenium, platinum/rhenium, palladium/ruthenium, palladium/rhenium, cobalt/palladium, cobalt/platinum, cobalt/chromium, cobalt/ruthenium, silver/palladium, copper/palladium, nickel/palladium, gold/palladium, ruthenium/rhenium, and ruthenium/iron.

16. The process of claim 1, further comprising wherein the acetic acid is formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

17. A process for recovering ethanol, comprising:
hydrogenating acetic acid in an acetic acid feed stream in the presence of a catalyst to form a crude product;
separating at least a portion of the crude product in a first column into a first distillate comprising one or more $C_{2+}$ alcohols and ethyl acetate, and a first residue comprising acetic acid;
separating at least a portion of the first distillate in a second column into a second distillate comprising ethyl acetate and a second residue comprising one or more $C_{2+}$ alcohols; and
separating at least a portion of the second residue in a third column into a third distillate
comprising ethanol, and one or more sidedraws comprising one or more $C_{3+}$ alcohols.

18. The process of claim 17, wherein said one or more $C_{3+}$ alcohols are selected from the group consisting of isopropanol, n-propanol, n-butanol, 2-butanol, isobutanol, tert-butanol, 2,2-dimethyl-1-propanol, 3-pentanol, 2-pentanol, 1-pentanol, 3-methyl-2-butanol, 2-methyl-2-butanol, a mixture thereof, and an azeotrope thereof.

19. The process of claim 17, wherein said first distillate comprises said one or more $C_{2+}$ alcohols in an amount from 20 to 95 wt. % and, wherein said one or more $C_{2+}$ alcohols comprises from 90 to 99.9 wt. % ethanol and from 0.001 to 10 wt. % of said one or more $C_{3+}$ alcohols.

20. The process of claim 17, wherein said first distillate comprises said one or more $C_{2+}$ alcohols in an amount from 20 to 95 wt. % and, wherein said one or more $C_{2+}$ alcohols comprises from 90 to 99.9 wt. % ethanol and from 0.001 to 10 wt. % of said one or more $C_{3+}$ alcohols.

21. The process of claim 17, wherein said second residue comprising said one or more $C_{2+}$ alcohols comprises from 0.001 to 10 wt. % of said one or more $C_{3+}$ alcohols.

22. The process of claim 17, wherein the third distillate comprises less than 1000 wppm of said one of more $C_{3+}$ alcohols.

23. A process for recovering ethanol, comprising:
providing a crude product comprising ethanol, acetic acid, water, and one or more $C_{3+}$ alcohols, wherein the concentration of the one or more $C_{3+}$ alcohols is less than 8 wt. %;
separating at least a portion of the crude product into an intermediate stream comprising ethanol and one or more $C_{3+}$ alcohols, and a residue comprising acetic acid; and
separating at least a portion of the intermediate stream in a column into a product distillate comprising ethanol, one or more sidedraws comprising one or more $C_{3+}$ alcohols, and a residue comprising water.

* * * * *